United States Patent [19]

Wagner et al.

[11] Patent Number: 5,135,483

[45] Date of Patent: Aug. 4, 1992

[54] ATHERECTOMY DEVICE WITH A REMOVABLE DRIVE SYSTEM

[75] Inventors: Erik J. Wagner, Coral Springs; Vincent J. Jannetty, Plantation, both of Fla.

[73] Assignee: Dow Corning Wright Corporation, Arlington, Tenn.

[21] Appl. No.: 734,380

[22] Filed: Jul. 22, 1991

[51] Int. Cl.[5] .............................................. A61B 17/32
[52] U.S. Cl. ...................................... 604/22; 606/170; 128/751
[58] Field of Search ............... 604/22; 606/167, 168, 606/169, 170, 171, 172, 173, 174; 128/751, 752, 753, 754, 755, 756, 757, 758, 759

[56] References Cited

U.S. PATENT DOCUMENTS

| | | | |
|---|---|---|---|
| 3,623,474 | 11/1971 | Heilman et al. | 128/2 R |
| 3,701,345 | 10/1972 | Heilman et al. | 128/2 R |
| 4,024,864 | 5/1977 | Davies et al. | 128/214 F |
| 4,696,667 | 9/1987 | Masch | 604/22 |
| 4,700,470 | 10/1987 | Muller | 29/798 |
| 4,747,406 | 5/1988 | Nash | 128/305 |
| 4,812,724 | 3/1989 | Langer et al. | 318/599 |
| 4,854,324 | 8/1989 | Hirschman et al. | 128/655 |

Primary Examiner—C. Fred Rosenbaum
Assistant Examiner—M. Mendez
Attorney, Agent, or Firm—John L. Chiatalas

[57] ABSTRACT

An intravascular catheter comprises an elongated flexible jacket having opposed proximal and distal ends and a central passageway extending between the ends. A working head is located at the distal end, including a canalizing tip and a bearing for rotatably supporting the tip on the working head to remove occlusions from the lumen of a vessel. A drive cable extends through the central passageway and has a driving portion operatively located adjacent the distal end and a driven portion for releasably engaging the working head located opposite the driving portion. A power-driven motor is coupled to the driven end for rotating the cable. The jacket segments are disconnected and the canalizing tip removed with the drive cable from the catheter and replaced with a guide wire which is inserted through the central passageway.

28 Claims, 8 Drawing Sheets

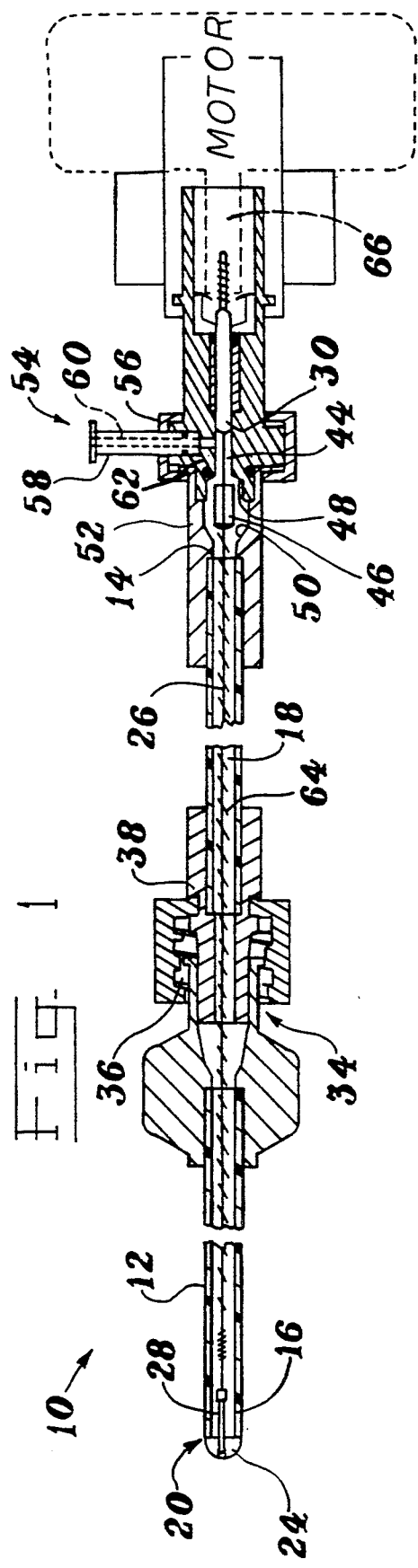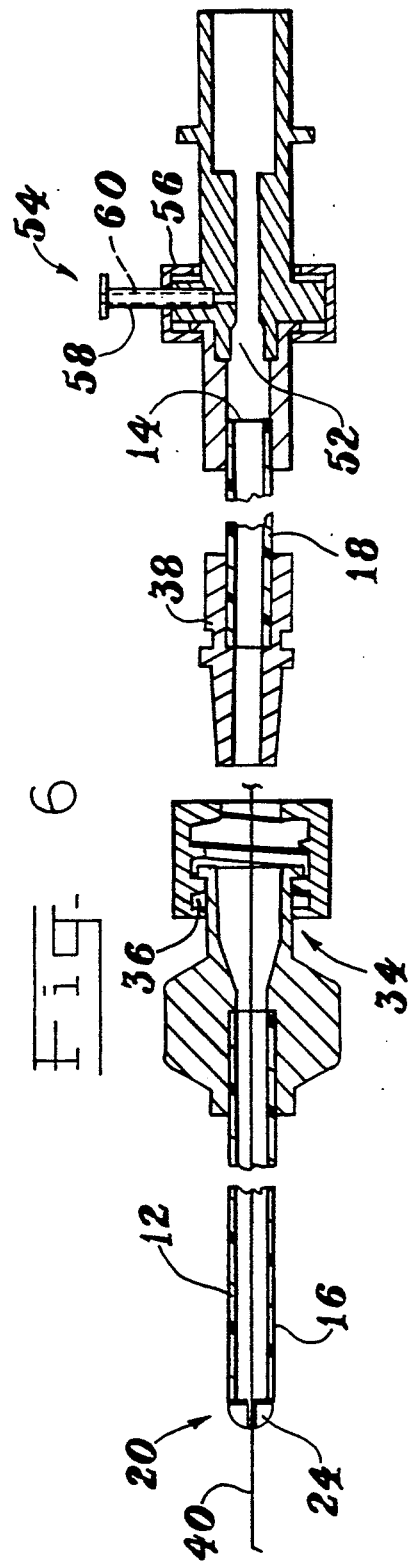

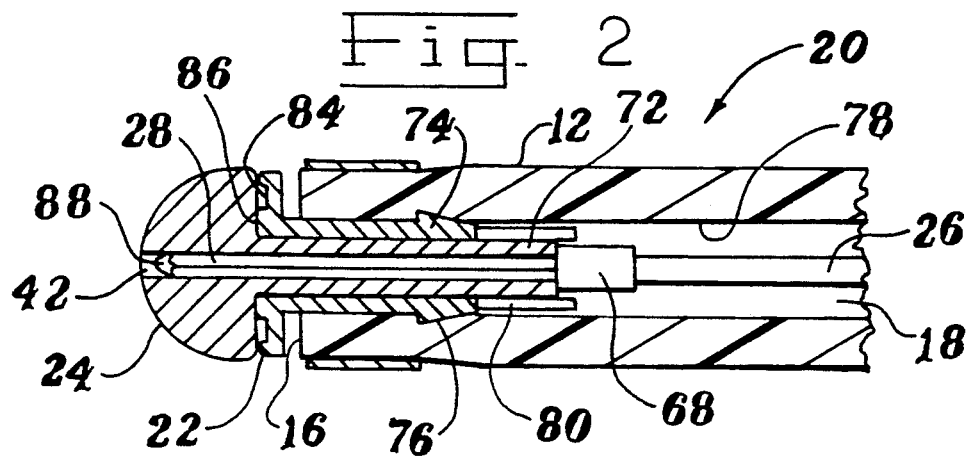
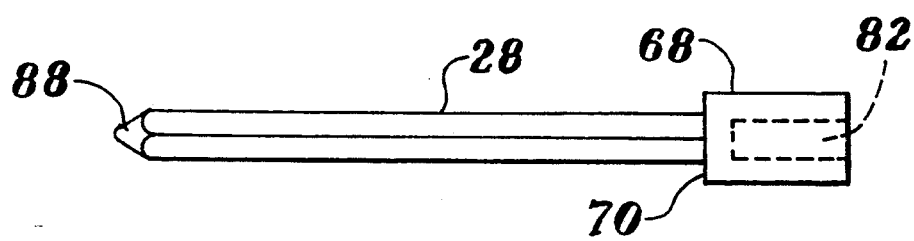
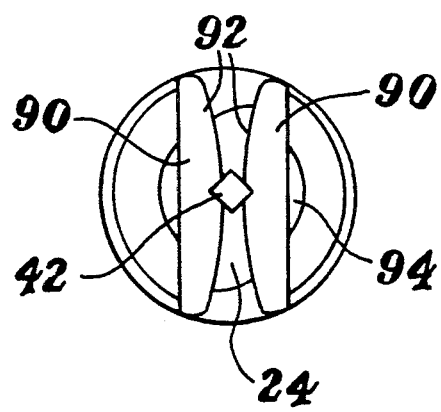 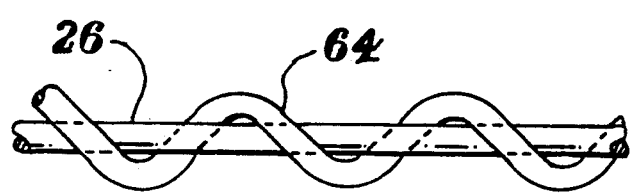

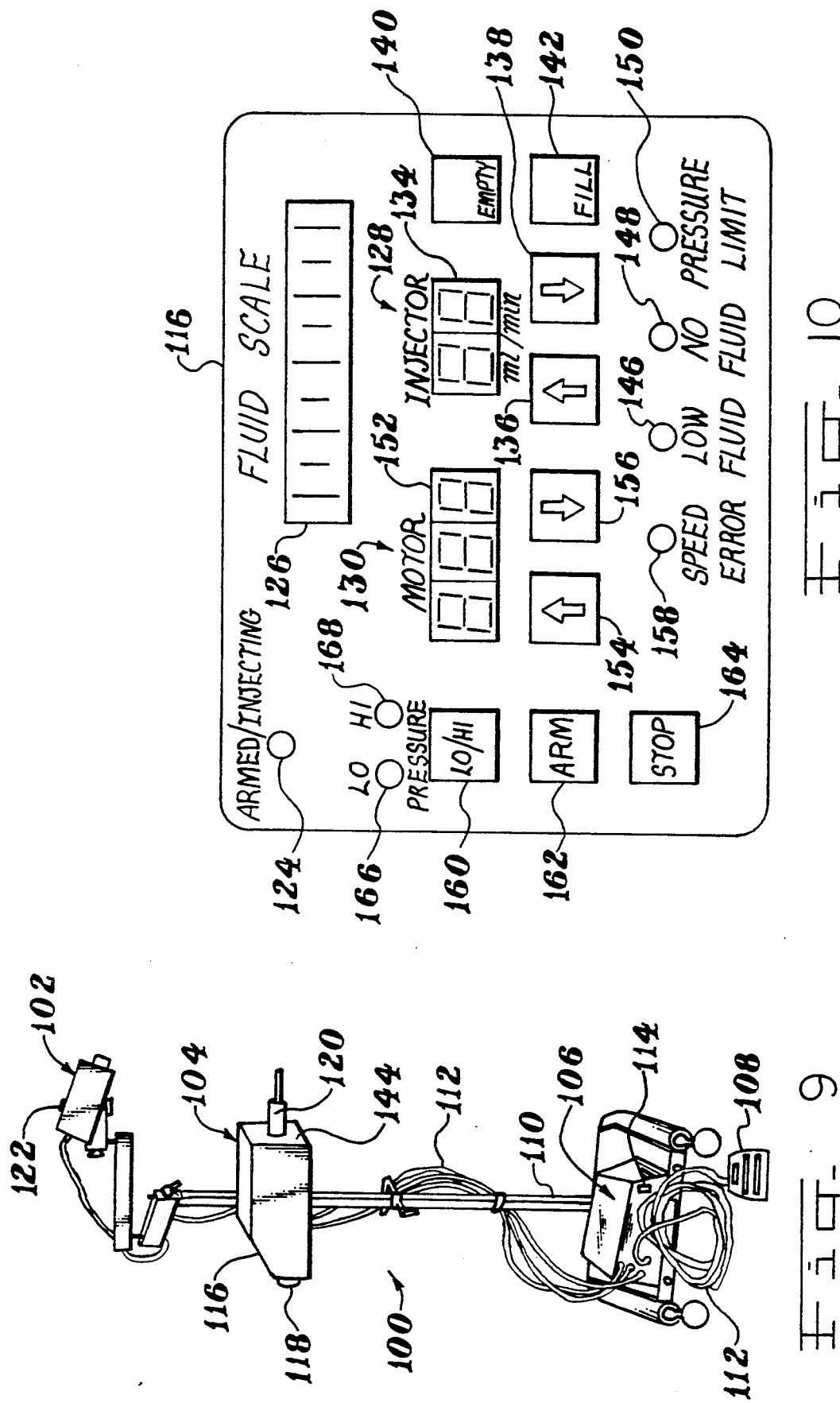

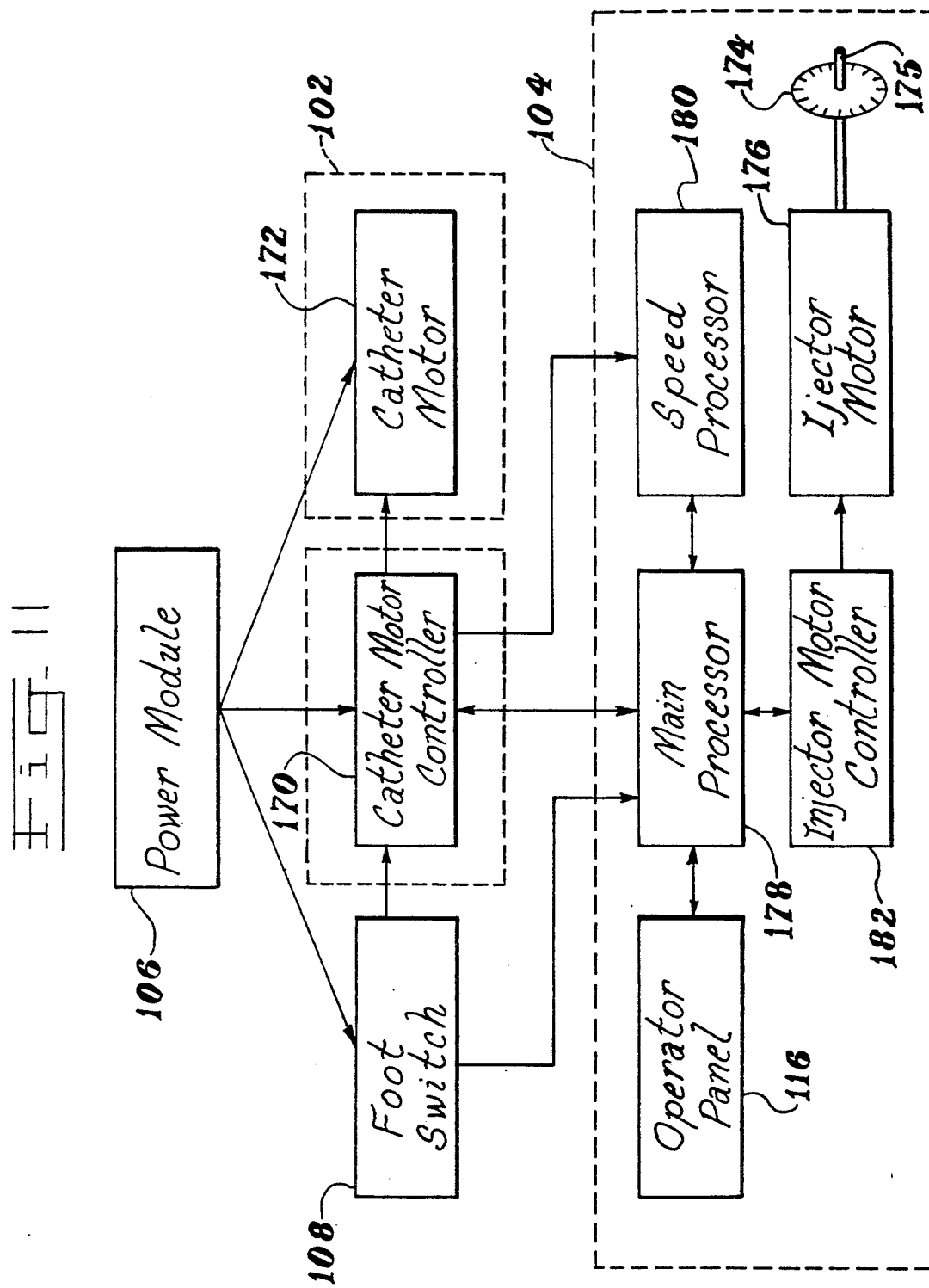

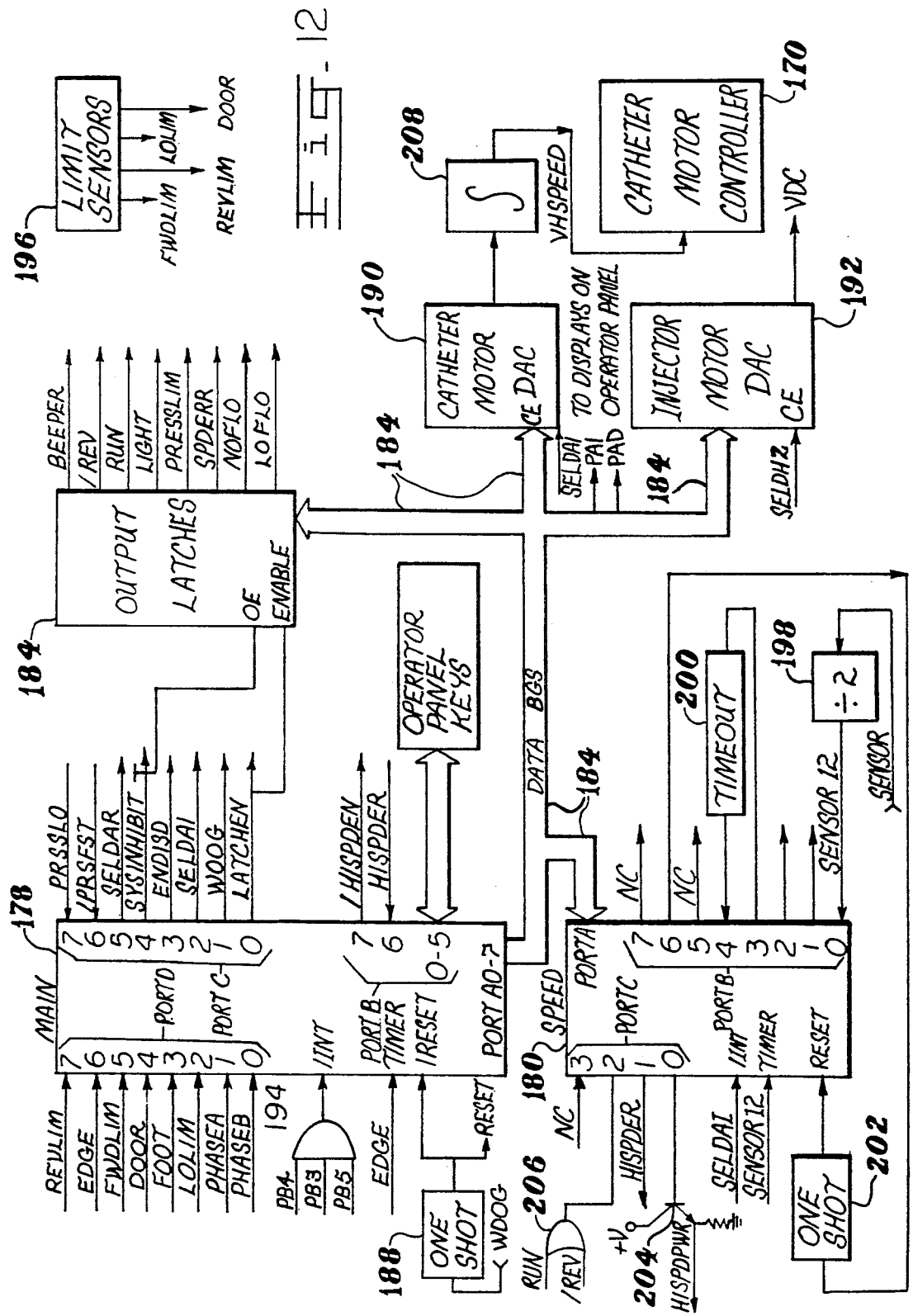

ATHERECTOMY DEVICE WITH A REMOVABLE DRIVE SYSTEM

BACKGROUND OF THE INVENTION

1. Field of the Invention

The invention relates generally to intravascular catheters, particularly catheters having a rotating tip, useful in removing in occlusions from a vessel, such as an artery or vein.

2. Description of the Prior Art

During an atherectomy procedure using a rotating catheter, it is often necessary and desirable to route the catheter through a vessel along a guidewire which has been, in turn, threaded through the center of the catheter and partially through the lumen of the vessel. Further, it is desirable to keep the catheter tube located in the vessel following atherectomy to allow threading of the guidewire into and out of the catheter tube; moreover, it is desirable to leave the catheter tube in place without removing it from the vessel in order to change from an atherectomy catheter to a diagnostic device or balloon catheter. Unfortunately, conventional rotating catheters that do not have a guidewire cannot be used for such exchange because they are solid, therefore, no simple easy means exist for providing the desired exchange function.

One approach of conventional devices is found in U.S. Pat. No. 4,696,667 to Masch, which discloses an intravascular catheter including a flexible guidewire housed within a flexible hollow tubular drive member. The tubular drive member is originally attached to a working head at the distal end of the tube and is driven at the proximal end of the tube by a drive assembly. The drive assembly is composed of a series of gears that engage and rotate the tubular drive member. The tubular drive member is stationary and cannot be removed.

Another example is U.S. Pat. No. 4,747,406 to Nash, which discloses a flexible elongated tubular catheter having a tool which rotates at relatively high speeds, for example, 20,000 rpm, located at the distal end of the catheter. The tool used has a central opening and is rotated by a hollow wire drive shaft.

In other catheters of the "Kensey" type, a central passageway in the drive shaft aligns with the central opening of the cutting tool to accept a conventional guidewire. Thus, although the catheter tube can be threaded along a guidewire during the cutting operation, the drive assembly is not removable.

A specific concern to which intravascular therapy has been directed is acute pulmonary thrombosis, a life-threatening condition that is difficult to diagnose and treat. Acute thrombosis can occur in many areas of the vascular system, causing reduced hemodynamic flow and potential problems for the patient. Although current techniques exist for treating thrombosis, each possess drawbacks rendering them overly time-consuming and risky, with limited effectiveness.

Several drug therapies have been proposed for treatment of thrombus, for example, blood thinners such as Streptokinase, Urokinase and Tissue Plasminogen Activator (TPA), and have been found useful in reducing thrombus in patients. However, a disadvantage of this approach is that these drugs are slow-acting agents, which in acute conditions like pulmonary thrombosis means that patients do not live long enough for the drug to work. Although at increased dosages the results are somewhat faster, the incidence of internal bleeding becomes a negative factor.

Surgical removal of thrombus-affected vessels has also been performed, but this procedure is much more invasive than drug therapy. Moreover, certain areas of the body are more hazardous for this procedure, further increasing patient risk.

A balloon technique has been utilized for certain thrombus-laden vessels, for example, in the lower extremities. In the legs, a deflated balloon is passed below the desired treatment area, then inflated and withdrawn, pulling debris up with the balloon. A disadvantage of this technique is the hazard of unremoved thrombus chunks flowing upstream and lodging in the vessel lumen.

A "Kensey" type of recanalization catheter has also been studied for use as an interventional approach to thrombosis, for example, an 8 French catheter has been developed by Drs. Kensey and Nash. Although such devices have been found capable of thrombus ablation, they lack diagnostic capabilities and are difficult to maneuver to the correct location. Further, the exposed tip of the catheter has the potential for causing trauma in tight-fitting locations.

An aspirating, low-speed mechanical catheter for percutaneous thrombectomy has also been proposed, e.g., U.S. Pat. No. 4,700,470, using an internal propeller for pulling thrombus in and an external vacuum source to pull debris out through the catheter. Again, neither diagnostic capability nor maneuverability assistance is provided.

In the past, when physicians have had to operate both a rotating catheter device and a fluid dispenser device as a single unit, it was necessary to operate two separate and independent controllers. In other words, a dedicated motor controller was used to control the speed of rotation of the catheter tip and a separate fluid controller was used to control the amount of fluid dispensed, and the two controllers communicated through a separate interface. The operator of such a dual system must be highly trained in order to properly monitor both systems. Further, since the fluid controller system is a general purpose controller system, it provides certain functions that are unneeded for a rotating tip, fluid ejecting catheter device. Hence, the resulting system is far more complex than actually needed and accordingly, more expensive than required.

Examples of prior art catheter motors and motor controller systems include the system manufactured by E.T.I. Norland Corporation, of Fort Atkinson, Wis. under part number TW1. Examples of prior art fluid control systems include the systems shown in U.S. Pat. No. 4,854,324 in the name of Alan D. Hirschman et al and entitled, "Processor Controlled Angiographic Injector Device"; U.S. Pat. No. 4,812,724 in the name of Alois A. Langer et al and entitled, "Injector Control"; U.S. Pat. No. 4,024,864 in the name of Gomer L. Davies et al and entitled, "Injector With Overspeed Protector"; U.S. Pat. No. 3,701,345 in the name of Marlin S. Heilman et al and entitled, "Angiographic Injector Equipment" and U.S. Pat. No. 3,623,474 in the name of Marlin S. Heilman and entitled, "Angiographic Injection Equipment".

Accordingly, there still remains a need for an interventional instrument that percutaneously enters the body and is capable of selective diagnosis when sufficiently close to an affected area of the vascular system, particularly such a device which is useful in evaluating and treating acute thrombosis.

There is also still a need for a rotating intravascular catheter which has a removable drive system for allowing a catheter to remain in place in the vessel of a lumen so that a drive assembly and the guidewire may be interchangeably routed through the center of the catheter.

There is also a further need for an improved combination rotational motor and fluid infusion controller for catheters having rotating tips, which can be effectively manipulated by a single operator during an intravascular surgical procedure.

SUMMARY OF THE INVENTION

According to one aspect of the invention, there is provided an intravascular catheter comprising an elongated flexible jacket having opposed proximal and distal ends and a central passageway extending between the ends. A working head is located at the distal end of the jacket, with a canalization tip rotatably supported on the working head. A drive cable extends through the central passageway and has a driving portion operatively located adjacent the distal end and a driven portion located opposite the driving portion. Means are provided for rotating the cable at the driven end and means are provided for releasably coupling the driving portion of the cable to the working head to rotate the cutting tip, wherein the drive cable may be uncoupled from the working head and removed from the jacket.

BRIEF DESCRIPTION OF THE DRAWINGS

The invention may be better appreciated by reference to the attached Drawings, which illustrate one or more preferred embodiments, wherein:

FIG. 1 is a sectional view of a catheter according to the invention, showing the removable connection of the drive assembly to the working head, as well as the preferred to the quick-disconnect of the drive cable to the means for rotating the drive cable;

FIG. 2 is an enlarged sectional view of the working head, showing the releasable connection between the cutting tip and the drive cable of the invention;

FIG. 3 is an enlarged view of the torque-transmitting distal end of the drive cable, adapted for rotating the cutting tip of the invention;

FIG. 4 is an end view of the cutting tip, with the drive assembly inserted into the central passageway of the invention;

FIG. 5 is an external view of the preferred helical bearing which surrounds the drive cable;

FIG. 6 is a sectional view of the catheter shown in FIG. 1 except that the drive assembly has been replaced by a guidewire extending through the central passageway of the invention;

FIG. 9 shows a perspective view of the control system for controlling the catheter motor and fluid injector motor coupled to control the operation of the catheter shown in FIG. 1;

FIG. 10 illustrates the control panel for the system shown in FIG. 9;

FIG. 11 shows a block diagram of the control system of FIG. 9;

FIG. 12 shows, primarily in block format, a more detailed diagram of the two processors and their associated circuits used to control the catheter motor and fluid injector motor;

DETAILED DESCRIPTION

Figure 8:
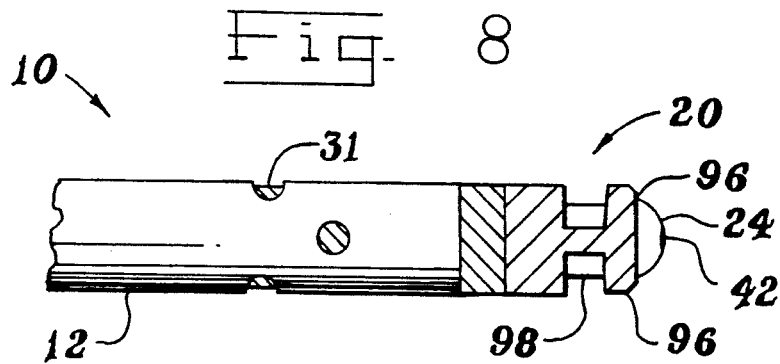
FIG. 8 is an enlarged view of the distal end of the catheter jacket shown in FIG. 7, showing the shrouded tip and infusion ports in greater detail, in a preferred aspect of the invention.

Referring to FIGS. 1-2, an intravascular catheter, generally shown at 10, comprises an elongated flexible jacket 12 having opposed proximal 14 and distal 16 ends, defining a central passageway 18 extending between and innerconnecting the ends. A working head, generally indicated at 20, is located at the distal end 16 of the jacket 12 and preferably includes bearing means 22 for supporting a rotatable tip 24 on the working head. A flexible drive cable 26 extends through the central passageway 18 and has a driving portion 28 releasably connected to the working head 20 and a driven portion 30 operatively connected to a source of high-speed rotary motion. The cable 26 is removable from the central passageway 18 of the jacket 12 once the driving portion 28 has been disconnected from the working head 20.

Referring to FIGS. 1-6, a releasable coupling is provided, preferably a luer lock mechanism 34 for releasably coupling and uncoupling the driving portion 28 of cable 26 from the working head 20. Specifically, the quick-disconnect coupling mechanism 34 further comprises a male portion 36 which interlocks with a female portion 38, both male 36 and female 38 portions being integral with the jacket 12. The quick-disconnect mechanism 34 operates as a twist-off coupling allowing the jacket to be separated at the coupling 34 and the drive assembly removed (FIG. 1) and replaced with a guidewire 40, as shown in FIG. 6. As shown in FIG. 2, the tip 24 functions integrally with the working head 20 because the bearing sleeve 22 is press fit into the central passageway 18. The tip 24 has a central guideway 42 which alternately receives the driving end 28 of the cable 26 to rotate the tip and, when the cable is withdrawn from the central passageway, allows guidewire 40 to pass through the guideway 42 (FIG. 6).

Referring to FIG. 5, the drive cable 26 preferably is made of a flexible solid wire which, as shown in FIGS. 1 and 6, extends through the central passageway between the proximal 14 and distal 16 ends of the jacket 12. The driven end 30 which is coupled to the powerized source further comprises a larger diameter portion 43 which press fits into a narrowed throat 44 formed in the central passageway 18 adjacent the proximal end 14 of the jacket 12. A stop block 46 on the driven end 30 is provided to limit axial movement of the cable, the block 46 abutting a proximal shoulder 48 and a distal shoulder 50 of a widened centering portion 52 adjacent the proximal end 14 of the jacket 12.

Figure 7:
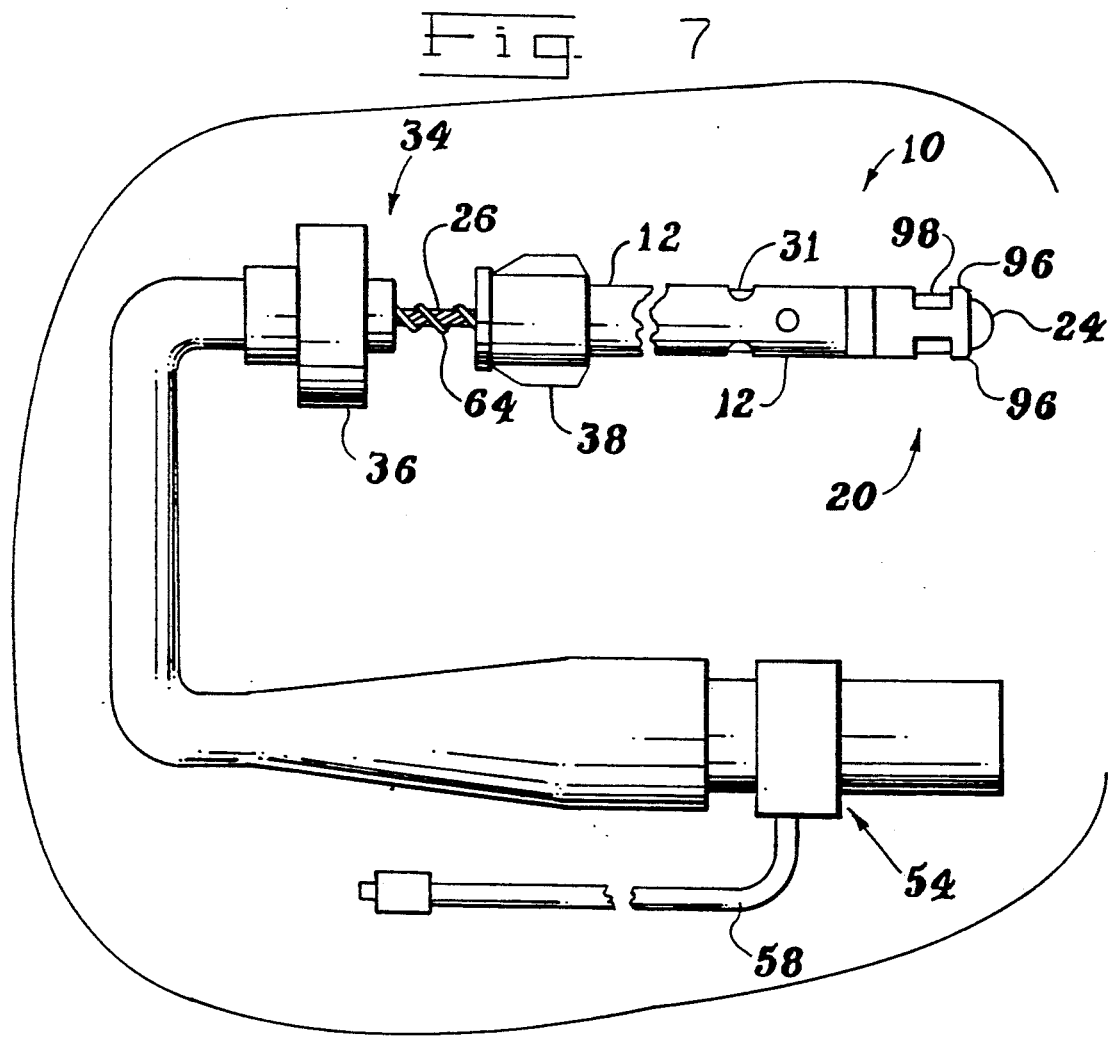
FIG. 7 is an external perspective view of a thrombectomy catheter, showing especially the drive assembly and infusion ports of the invention.

Referring further to FIGS. 1 and 6-7, a source of injectable fluid supplies a radiopaque liquid to central passageway 18 of jacket 12 through port 54. The port 54 is connected to a housing 56 which receives an injection tube 58 having a lumen 60 (shown in phantom) that opens into a delivery port 62 leading, in turn, into the throat 44 of the central passageway 18. The radiopaque fluid injected through the channel 62 travels toward the distal end 16 of the jacket 12 through the central passageway 18, exiting from the high volume infusion ports 31 into the lumen of a vessel. It should be understood that additional infusion of fluid may occur by seepage through various articulating surfaces of the working head 20, however, such a flow path is much more restricted compared with the much greater infusion capacity achieved through ports 31. The drive cable 26 is made of small diameter wire and is further surrounded by an elongated helically-wound bearing 64, around which is wound an elongated helical bearing 64 taking the form of a wire coil surrounding cable 26. The helical bearing 64 prevents the metal cable 26, when rotating, from frictionally contacting the relatively softer plastic material of jacket 12, particularly when the jacket is bent, as often occurs in conforming to the convoluted path of a vessel lumen. The helically-wound bearing 64 is removable from jacket 12 along with the drive cable 26 as a single assembly. The widened portion 30 of the drive cable 26 which, in operation, is situated adjacent proximal end 14 of jacket 12, is coupled to a drive shaft 66 powered by the appropriate source of rotary motion.

Referring to FIGS. 2-4, the driving pin 28 of cable 26 has a chuck 68 which includes a shoulder 70 for abutting the end of a shaft 72 which is integral with the tip 24. As mentioned previously, the bearing sleeve 22 extends within the central passageway at the distal end 16 of jacket 12. Bearing sleeve 22 is snapped into place axially on the distal end 16 of jacket 12 by locking barb 74 which engages a corresponding groove 76 formed in the internal surface 78 of the jacket 12. A retaining sleeve 80 extends proximally from barb 74 to center the chuck 68 in abutment with the bearing sleeve 22. Chuck 68 has an internal fitting 82 into which an end of drive cable 26 is welded in place. Bearing sleeve 22 contains an annular groove 84. The driving pin 28 of cable 26 has a spiked apex 88 extending partially into guideway 42 of tip 22. Driving pin 28 has an irregular, preferably rectangular transverse cross section, which mates with that of guideway 42, such that the driving pin 28 of the cable 26 transmits torque to the guideway 42 for rotating the tip 24 at high speeds.

FIG. 4 shows tip 24 in greater detail, with a pair of flattened hemispherical sides 90 defining a pair of arcuate cutting edges 92 which converge centrally on guideway 42. As will be appreciated, there still remains a relatively limited fluid path for seepage of infused liquid through the guideway via openings between adjacent articulating surfaces, as indicated by numeral 94.

Referring to FIGS. 6-7, there is shown a preferred embodiment of the catheter 10 designed specifically for diagnosis and treatment of life-threatening acute pulmonary thrombosis. The jacket 12 is particularly well-suited for the tortuous branches of the lung; however, it is also adaptable to other vascular thrombosis. The tip 24 functions as a high-speed rotary impeller and has a rounded shape, surrounded by a shroud 96 affixed to the working head 20 of an 8 French flexible catheter jacket 12. In this respect, the tip 24 functions to homogenize the thrombus. Shroud 96 has a plurality of relatively wide longitudinal slots 98, although circular or oral openings (not shown) could be used. The shroud 96, designed to present a smooth exterior to the vessel lumen, is of relatively thin metal, with smooth edges which shield the vascular tissue from the tip and avoid trauma to the vessel wall, compared with the prior art structures alluded to above. A guide wire (not shown) can be used for tracking the catheter through the lumen, as explained above with reference to the other Figures.

Fluid is injected through the ports 31 preferably by manual delivery (see below), with the drive cable 26 removed to allow unobstructed flow through the central passageway 18 as shown in FIG. 6. Where higher delivery rates are required, e.g., greater than 10-60 ml./min., a special injector tube can be coupled to the jacket 12 via a standard luer fitting, rather than the proximal segment of jacket 12.

The inventors have found, through experimentation on simulated thrombus-laden vessels, e.g., using food gelatin, that a slight protrusion of the tip 24 distally past the shroud 96 is desirable to "pull" thrombus into the impeller tip 24 and break it up quickly, functioning as a combination pump/blender. A smaller 8 French "introducer" catheter is adequate for subcutaneous placement in the vessel through a correspondingly smaller puncture site, eliminating any need for a larger guide catheter. A pair of the ports 31 may be laterally opposing, i.e., 180 degrees apart, with another pair of laterally opposing ports spaced proximally and offset 90 degrees from the first pair of ports 31. Although the fluid injector system described relative to FIGS. 9-15 (below) is typically adequate for thrombectomy procedures involving the peripheral vessels in non-life threatening situations, a higher volumetric rate is needed for pulmonary thrombolysis, particularly in the medium-to-large branches where manual injection into tube 58 through port 54 is required at rates from 0.1-20 ml./sec. depending on x-ray sensitivity.

Referring now to FIG. 9, a perspective view of the control system 100 for controlling the catheter motor system 102 and fluid injector system 104 coupled to control the operation of the catheter 10, is shown in FIG. 1. The control system 100 is used in atherectomy and some thrombolysis applications. More specifically, control system 100 controls and drives the rotation of tip 24 and provides a controlled flow of fluid through guideway 94 (FIG. 4) of catheter 10. Catheter motor system 102 is capable of rotating tip 24 at a velocity of up to 100,000 revolutions per minute and fluid injector system 104 controls the flow rate of fluid flowing into catheter 10, which fluid may be used, among other things, to cool and lubricate tip 24. In addition, system 100 includes a power module 106, foot switch 108, a pedestal 110 used to hold catheter motor system 102, fluid injector system 104 and power module 106 and a series of cables 112 connecting power module 106 to foot switch 108, catheter motor system 102 and system 104.

It should be understood that for most indications, the fluid injector 104 is adequate for infusion of peripheral vessels, even in thrombolysis, but manual injection, at higher rates than provided by injector 104, is needed in some applications where rate of delivery is critical to patient survival. Such situations include pulmonary thrombolysis, especially in medium to large branches.

Power module 106 provides low voltage DC power to the catheter motor system 102, fluid injector system 104 and foot switch 108. Module 106 includes a power switch 114 for shutting off the AC power provided to power module 106.

Fluid injector system 104 is designed to operate at pressures up to 150 pounds per square inch and the flow rate of the fluid therefrom is adjustable from ten to sixty milliliters per minute, in steps of five milliliters per minute. A system control panel 116, seen in detail in FIG.

10, is placed on the cover of fluid control system 104 and may be used by an operator to control both the velocity the rotating tip 24 and the fluid flow through catheter 10. Panel 116 will be described in detail hereafter with respect to FIG. 10. Fluid control system 104 also includes a knob 118 for manually controlling the fluid flow of the syringe 120 plunger included in system 104, which other wise is controlled by an electric motor.

Catheter motor system 102 includes the catheter motor and a motor control unit therefor. The motor is a three phase, two pole brushless DC motor controllable by a control unit in steps of 5000 rpm up to a maximum of 100,000 rpm. Catheter motor system 102 also contains a fan (not shown) and a ready indicator lamp 122, which flashes at a low rate when the motor is ready to operate and at a faster rate when the motor is operating. Catheter motor system 102 may be purchased from Harowe Servo Controls, Inc. of West Chester, Pa. as part number B111OH1495 for the motor and as part number CNT3605F001 for the associated motor controller.

Foot switch 108 is a two pole switch which, when depressed, operates both the catheter motor system 102 and the fluid injector system 104. When foot switch 108 is initially depressed, the motor in fluid injector system 104 begins operating and approximately two to four seconds later, the motor in catheter motor system 102 begins operating. This delay insures fluid is flowing prior to catheter motor operation so that tip 24 is not damaged.

Referring now to FIG. 10, the operator panel 116 is shown. The Armed/Injecting light 124 is illuminated whenever foot switch 106 is depressed. Fluid scale 126 indicates the amount of fluid remaining in syringe 120. The remaining portion of panel 116 is divided into three sections, the injector control section 128, the motor control section 130 and the additional control section 132. The injector control section 128 includes a two digit display 134 which shows the programmed flow rate in milliliters per minute (ml/min). The flow rate is programmed by pressing one of the keys 136 or 138, which respectively increases (key 136) or decreases (key 138) the flow rate. Two additional keys, Empty key 140 and Fill key 142, are used to either empty or fill syringe 120. When the Empty key 140 is pressed and held, the syringe 120 plunger moves forward and ejects any fluid in syringe 120 and when the Empty key 140 is released, the plunger stops. A door 144, which provides support for syringe 120 (seen in FIG. 9), must be closed to permit Empty key 140 to operate. When Fill key 142 is pressed, the syringe 120 plunger moves backwards and syringe 120 is filled. Fill key 142 is active regardless of whether door 144 is open or closed. The syringe 120 plunger must be fully retracted in order for syringe 120 to be removed. An injector motor and its associated controller (described hereafter) controls the movement of the plunger of syringe 120.

In addition, injector section 128 includes three lights, a Low Fluid light 146, a No Fluid light 148 and Pressure Limit light 150. The Low Fluid light 146 is illuminated when the amount of fluid in syringe 120 reaches the 30 milliliter level and the No Fluid light 148 becomes illuminated when the amount of fluid in syringe 120 reaches the 5 milliliter level. The Pressure Limit light 150 becomes illuminated if the fluid injector system 104 pressure reaches 150 pounds per square inch while injecting fluid. If the pressure limit is reached, the system automatically shuts down. For each of the lights 146, 148 and 150, a beeper (not shown) may be sounded to provide further warning.

The motor control section 130 is used to control the speed of catheter motor system 102 and includes three digit display 152, a pair of keys 154 and 156 and a Speed Error light 158. Display 152 displays the programmed, or desired, speed of the catheter motor of catheter motor system 102 (in thousands of rpm's), as set by operating keys 154 and 156. Specifically, to increase the programmed speed of the motor in catheter motor system 102, as displayed on display 152, key 154 is pressed and to decrease the speed of the motor in catheter motor system 102, as displayed on display 152, key 156 is pressed. If the actual speed of the motor of catheter motor system 102 differs by more 5000 rpm for more than one and one half seconds, then light 158 becomes illuminated, thereby indicating a speed error condition. Thereafter, the control system automatically reduces the speed of the motor in catheter motor system 102 to zero.

The additional control section 132 includes three keys, a Lo/Hi key 160, an Arm key 162 and a Stop key 164, and two pressure indicator lights, a Lo light 166 and a Hi light 168. Lo/Hi key 160 is used to toggle between the low and high pressure limits of fluid injector system 104. If only a single pressure limit is used, then both the low and high pressure values may be set to be the same value, or Lo/Hi key 160 may be disabled. Arm key 162 is pressed to activate the fluid injector system 104 and when system 104 is armed, the Empty key 140 and Fill key 142 are rendered inactive and the Armed/Injecting light 124 flashes. Footswitch 108 may be released when it is desired to stop the catheter motor system 102. Once power is removed from the catheter motor system 102, fluid injector system 104 stops and disarms, and the catheter motor system 102 and flow rate from fluid injector system 104 maintain their settings. Further, the Armed/Injecting light extinguishes and the Empty and Fill keys are reactivated. Alternatively, the Stop key 164 may be pressed to stop the catheter motor system 102, and this overrides the pressed footswitch 108. When Stop key 164 is depressed, the catheter motor system 102 and fluid injector system 104 return to the default settings.

Referring now to FIG. 11, an electrical block diagram of system 100 is shown. In FIG. 11, like numerical designations are used for components which are common with those shown by FIG. 9. As previously noted with respect to FIG. 9, the principal components of system 100 are catheter motor system 102, fluid injector system 104, power module 106 and foot switch 108. As further seen in FIG. 11, catheter motor system 102 includes a catheter motor controller 170 and a catheter motor 172. Catheter motor 172 may be a commercially available three phase, two pole brushless DC motor. Catheter motor 172 may additionally include a fan (not shown) and an elapsed time indicator (not shown) and provides encoder signals manifesting the actual speed of motor 172. Motor controller 170 also may be a commercially available pulse width modulated brush less motor controller, delivering a zero to 100,000 rpm control output.

Fluid injector system 104 includes operator panel 116, previously described with respect to FIG. 10, and injector motor 176, which may be connected to move the plunger of any commercially available 130 milliliter syringe having the appropriate barrel inside diameter.

Figure 15:
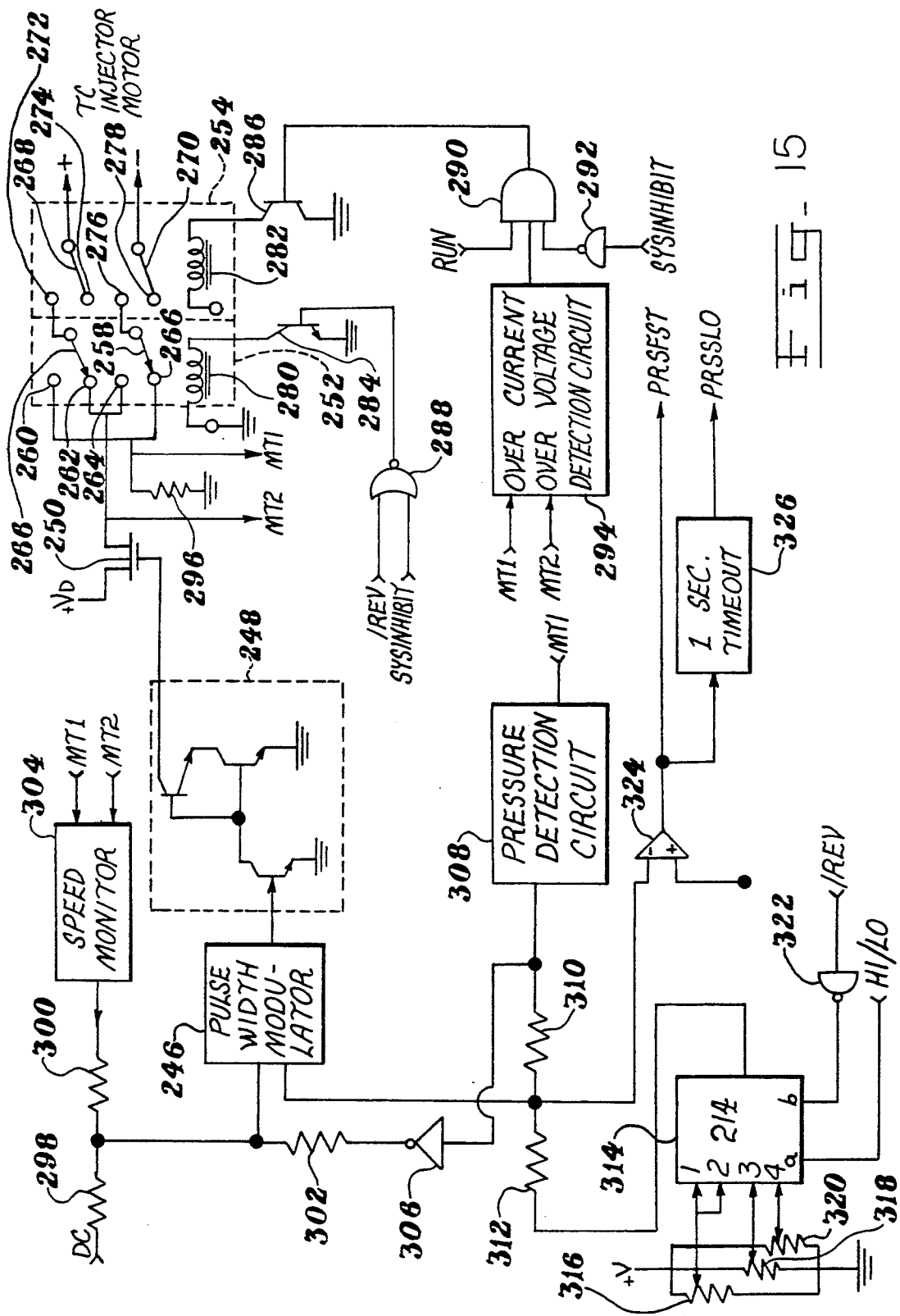
FIG. 15 shows, primarily in block diagram form, the catheter motor driver circuit.

An encoder disk 174 is attached to shaft 175 for providing signals manifesting the actual speed and direction of injector motor 176. In addition, fluid injector system includes a main processor 178 and a speed processor 180, which together control the overall operation of system 100, as will be described in detail hereafter. Further, an injector motor controller 182 is provided in fluid injector system 104 for providing appropriate pulse width modulated and other control signals to control the speed and direction of injection motor 176. Generally, the two processors 178 and 180, and their associated circuits are shown in more detail in FIG. 12 and the injector motor controller 182 is shown in FIG. 15.

In addition, power module 106 provides the power to each of the other blocks heretofore described in FIG. 11. It may include appropriated voltage regulators for converting ordinary line voltage (e.g. 120 volts AC) to the various voltages needed throughout system 100.

Referring now to FIG. 12, main processor 178 generally controls most functions in system 100 and speed processor 180 generally monitors the speed of catheter motor 172. Main processor may be a Motorola 68705U3 micro-controller with 112 bytes of RAM, 3776 bytes of EPROM, three I/O ports, labeled A, B and C and one input port labeled D. The following signals assignments are made for the four ports of main processor 178.

Port A, bits 0–7: Configured for output only. Port A is used as the data bus 184 to send 8 bits of parallel data to other components. In addition, lines 0 and 1 are used to send serial data to the displays 134 and 152 on operator panel 116, with line 0 being the data and line 1 being a clock signal.

Port B: Lines 0–2 and 7 are configured for output and lines 3–6 are configured for input. Specifically,
  Lines 0–5 are coupled to the various keys on operator panel 116 with lines 0–2 selecting a row and lines 3–5 reading the column of the selected row.
  Line 6, labeled HISPDER, when high, indicates a catheter motor 172 error. This signal is also used in handshaking operations.
  Line 7, labeled /HISPDEN, is used to enable and disable the catheter motor 172. When the line is high, the catheter motor 172 is disabled and when the line is low, the catheter motor 172 is enabled.

Port C: Lines 0–5 are configured for output and lines 6 and 7 are configured for input. Specifically,
  Line 0, labeled LATCHEN, is connected to enable latch 186, which also responds to the data bus 184 signals from port A. When LATCHEN becomes low the data then on the data bus 184 appears at the eight outputs of latch 186. These outputs then become the following signals, which are provided as indicated to accomplish the function set out:
    BEEPER causes an audible error sound;
    /REV, when low, indicates the injector motor 176 is to operate in the reverse direction;
    RUN, when high, indicates the injector motor 176 is to operate in the forward direction;
    LIGHT causes the Armed/Injecting light 124 to be illuminated;
    PRESS LIM causes the Pressure Limit light 150 to be illuminated;
    SPDERR causes the Speed Error light 158 to be illuminated;
    NOFLO causes the No Fluid light 148 to be illuminated; and
    LOFLO causes the Low Fluid light 146 to be illuminated.
  Line 1, labeled WDOG, is a signal provided at least once every 1.2 seconds during proper operation. It is used to toggle watchdog monostable multivibrator, or one-shot, circuit 188 prior to its 1.2 seconds timeout.
  Line 2, labeled SELDA1, is provided to the latch enable (LE) input of catheter motor digital to analog converter (DAC) 190. When the SELDA1 signal is low, the catheter motor DAC 190 reads the data provided thereto on the data bus 184. The SELDA1 signal and data 184 bus signals are similarly provided to speed processor 180.
  Line 3, labeled ENDISD, is used to enable display drivers within operator panel 116 to accept the serial information via data bus lines 0 and 1.
  Line 4, labeled SYSINHIBIT, when high, resets the displays, output latch 184, and injector motor relays shown in FIG. 15.
  Line 5, labeled SELDA2, is provided to the line enable (LE) input of injector motor digital to analog (D/A) converter 192.
  Line 6, labeled PRSFST, when high, manifests that the injector system 104 has reached its pressure limit.
  Line 7, labeled PRSSLO, when high, manifests that the injector system has been at the pressure limit for at least one second.

Port D has only input lines. Specifically,
  Line 0, labeled PHASEA, is used to manifest the state of channel A from encoder disk 174.
  Line 1, labeled PHASEB, is used to manifest the state of channel B from encoder disk 174.
  Line 2, labeled LOLIM, when low, manifests that the plunger of the fluid injector syringe 120 has reached the low fluid limit of 30 milliliters of fluid being left in syringe 120.
  Line 3, labeled FOOT, when high, manifests that the foot switch has been pressed.
  Line 4, labeled DOOR, when high, manifests that the syringe door 144 is open.
  Line 5, labeled FWDLIM, when low, manifests that the syringe 120 plunger has reached the forward limit switch, that is that the syringe is empty.
  Line 6, labeled EDGE, causes an interrupt on the rising edge whenever there is a change in states of the encoder 174 channels. This signal is low for about 50 microseconds on the raising or falling edge of either encoder channel A or B, and is discussed further with respect to FIG. 14.
  Line 7, labeled REVLIM, manifests that the syringe 120 plunger has reached its reverse direction limit.

In addition, main processor includes an interrupt input, labeled /INT, to which is coupled the output of AND gate 194. The keyboard column signals, PB3, PB4 and PB5 from operator panel 116 are provided as the three inputs of AND gate 194 and thus whenever a key on operator panel 116 is pressed, a signal causes an interrupt to occur in the execution of the program by main processor 178. Additionally, main processor 178 has an interrupt input to which is coupled the EDGE signal to detect motor movement, described above for Port D, Line 6. Finally, main processor 178 has a /RESET input to which the output of one shot 188 is coupled. If one-shot 188 is not reset at least every 1.2 seconds, it is assumed that main processor has "hung up", that is the program has entered into a loop from which it is unable to leave, and the output of one-shot 188 becomes high and resets main processor 178. It should be noted that the FWDLIM, REVLIM, LOLIM and DOOR signals provided to port D of main processor 178 are provided from various limit sensors 196 physically located throughout system 100.

Speed processor 180 is a Motorola MC68705P3 eight bit microprocessor having 112 bits of RAM, 1786 bits of EPROM, and two eight bit I/O ports A and B and a four bit I/O port C. The primary function of speed processor 180 is to monitor the speed of catheter motor 172 and stop operation if catheter motor is not operating within 5000 rpm of the programmed speed. The eight bits of Port A are configured as input ports designed to receive the data on data bus 184 in order that speed processor 180 is aware of the speed value sent to catheter motor DAC 190.

Port B of speed processor 180 has lines 0 and 4 configured as inputs and lines 3 and 6 configured as outputs. Lines 1, 2, 5 and 7 of port B are not used and are accordingly labeled N/C. The various lines of Port B are as follows:

Line 0, labeled SENSOR/2 is a sequence of SENSOR pulses that originate from a hall effect device in the catheter motor 172 and reflect the actual speed of the catheter motor 172; the SENSOR/2 signal is the SENSOR signal passed through a divide by two circuit 198.

Line 3 contains a high signal when a speed error is first detected and is provided to a timeout circuit 200.

Line 4 monitors to the output of to the output of timeout circuit 200 and when it becomes high, a speed error in catheter motor 172 is detected.

Line 6 is similar to the WDOG signal from port C, Line 1 of main processor 178 and is used to continually reset one shot circuit 202 once at least every 1.2 seconds.

Port C is configured such that lines 0 and 1 are outputs and line 2 is an input. Line 3 of port C is not used. The various signals of port C are:

Line 0 provides a signal through emitter follower transistor circuit 204 which is used to enable the catheter motor 172 to run. The signal is labeled HISPD PWR and motor 172 is enabled when it is high.

Line 1, labeled HISPDER, is provided as a high signal to main processor 178 when speed processor 180 detects a speed error with respect to catheter motor 172.

Line 2 manifests the result from OR gate 206, to which the /REV and RUN signals are provided. When line 2 becomes low, speed processor 180 is instructed to reset the speed error condition or to be prepared to accept information from main processor 178.

In addition to three ports, speed processor 180 has an interrupt input (/INT) to which is coupled the SELDA1 signal from main processor 178, a TIMER input to which the SENSOR/2 signal is coupled and a /RESET input to which the output of one shot 202 is coupled.

Both catheter motor controller 170 and injector motor controller 182 respond to the analog signals from DACs 190 and 192, respectively, and provide width modulated pulses to drive the motors 172 and 176. DACs 190 and 192, in turn, are enabled to respond to the data signal on data bus 184 when a respective one of the SELDA1 and SELDA2 signals are provided from main processor 178. The SELDA pulse is provided when a change to the catheter motor 172 speed is requested by main processor 178 and the SELDA2 signal is provided each time a change to the injector motor 176 speed is requested by main processor 178. The output of catheter motor DAC 190 is provided through an integrator circuit 208, to provide a smooth acceleration/deceleration to the catheter motor controller 170, which in turn provides three pulse width modulated signals to the three windings of catheter motor 172. The output of injector motor DAC 192 is provided as the VDC signal to injector motor controller 182, shown in more detail in FIG. 15.

Figure 13:
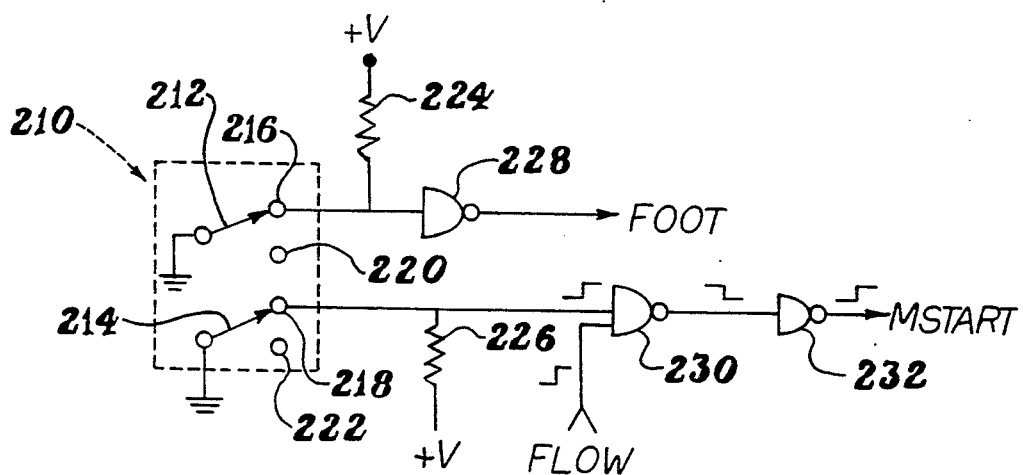
FIG. 13 shows the foot switch circuit.

Referring now to FIG. 13, an electrical schematic diagram of foot switch 108 is shown. Foot switch 108 includes double pole switch having two switch arms 212 and 214 each connected to electrical ground. As long as foot switch 108 is not pressed, the position of switch arms 212 and 214 is as shown connected to output terminals 216 and 218 respectively; when foot switch 108 is depressed, switch arms 212 and 214 move to contact terminals 220 and 222, which are otherwise unconnected. Terminal 216 is coupled to positive voltage +V through resistor 224 and terminal 218 is coupled to positive voltage +V through resistor 226. The junction of terminal 216 and resistor 224 is coupled through inverter 228 and is labeled as the FOOT signal, which is sent to processor 178 for the purpose of enabling operation of injector motor 176. After the injector motor has been operating for a couple of seconds, main processor 178 changes the state of the /HISPDEN signal to indicate that catheter motor 172 can begin operation. This signal together with the junction of terminal 218 and resistor 226 are provided through NAND gate 230 and inverter 232. The output from inverter 232 is the MSTART signal, which is provided to enable the pulse width modulators in catheter motor controller 170.

Figure 14:
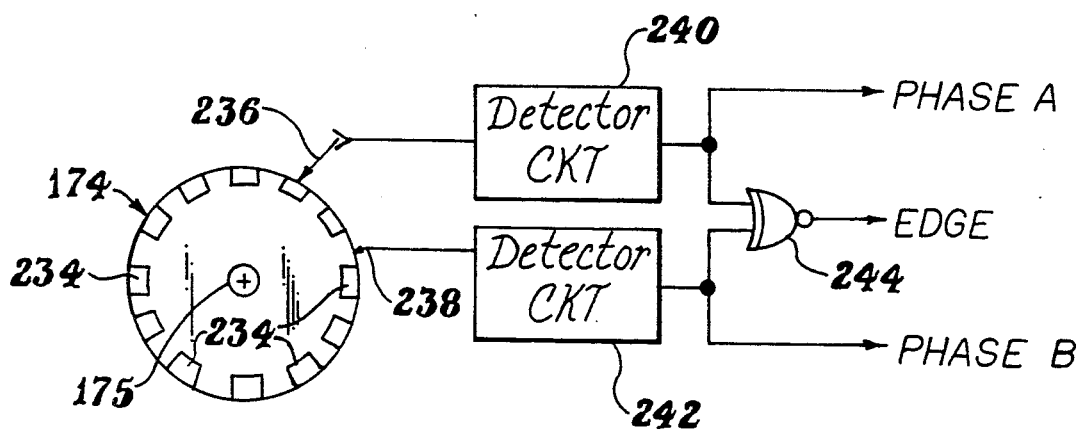
FIG. 14 shows the fluid motor direction monitoring circuit.

Referring now to FIG. 14, the manner of determining the speed and direction of the fluid injector motor 176 will be explained. As previously mentioned, encoder disk 174 is affixed to the output shaft 175 of injector motor 176. Encoder disk 174 includes a plurality, for example twelve, of magnetic material elements 234 evenly spaced about the peripheral edge thereof. A pair of magnetic detectors 236 and 238, such as hall effect devices, are positioned juxtaposed to encoder disk 174 so as to provide a signal whenever a magnetic element is aligned with a detector. These signals are then provided through detector circuits 240 and 242, which provide corresponding pulse shaped signals. Detectors 236 and 238 are positioned so as to be approximately 180° out of phase with one another, that is, they are positioned so that when one of detectors 236 or 238 is fully aligned with a magnetic element 234, the other of detectors 236 or 238 is fully aligned with the nonmagnetic space between elements 234. The output of detector circuits 240 and 242 are respectively the PHASEA and PHASEB signals. Both the PHASEA and PHASEB are provided as inputs to EXCLUSIVE NOR gate 144, the output of which is the EDGE signal.

As previously described, the PHASEA, PHASEB and EDGE signals are all provided to main processor 178 and in response to these signals, the speed and direction of fluid injector motor 176 can be determined. The EDGE signal is a pulse signal which is at twice the frequency of either of the PHASEA and PHASEB signals due the EXCLUSIVE NOR operation of gate 244. By looking at the relative phase difference between the PHASEA and PHASEB signals, that is whether the PHASEA signal leads or lags the PHASEB signal, the direction of injector motor 176 can be determined. This information is used by main processor 178 to determine when to provide the data to output latches 184, resulting in the provision of the RUN and /REV signals. These signals are, in turn, used by the injector motor controller 182 to control rotational direction of injector motor 176.

Referring now to FIG. 15, a more detailed diagram of injector motor controller 182 is shown. Pulse width modulator 146 provides pulses at a rate of 27 KHz having a duty cycle dependent upon the magnitude of the voltages applied thereto. Specifically, the voltages applied to pulse width modulator 246 will vary between about 0.5 volts to about 3.5 volts and the greater the voltage, the less the duty cycle of the modulated pulses at the output of pulse width modulator 246. Two different voltage control signals are applied as inputs to pulse width modulator 246 and the signal having the greater voltage controls the output.

The series of pulses at the output of pulse width modulator 246 are provided through drive circuit 248 to the gate electrode of power FET transistor 250 to render the source-drain path of transistor 250 conductive for the duration of each pulse. When FET transistor 250 is rendered conductive, the drive voltage $V_D$ is coupled through reverse relay 252 and run relay 254 to one of the forward (+) or reverse (−) terminal of injector motor 176. When voltage $V_D$ is coupled to the forward terminal (+), injector motor 176 runs in the forward direction causing fluid to be ejected from syringe 120 and into catheter 10 or to waste if the Empty key 140 is pressed. On the other hand, when voltage $V_D$ is coupled to the reverse terminal (−), injector motor 176 runs in the reverse direction so as permit the plunger to be returned to its home position and/or to fill syringe 120 if the Fill key 142 is depressed.

Reverse relay 252 includes two switch arms 256 and 258; switch arm 256 has two associated terminals 260 and 262 and switch arm 258 has two associated terminals 264 and 266. Similarly, forward relay 254 includes two switch arms 268 and 270; switch arm 258 has two associated terminals 272 and 274 and switch arm 270 has two associated terminals 276 and 278. Switch arm 256 is connected to terminal 272 and switch arm 258 is connected to terminal 276 to interconnect reverse relay 252 and forward relay 254. Switch arm 268 is connected to the forward terminal (+) of injector motor 176 and switch arm 270 is connected to the reverse terminal (−) of injector motor 176.

A relay coil 280, when current flows therethrough, is coupled to move switch arm 256 from terminal 262 to terminal 260 and switch arm 258 from terminal 266 to terminal 264. Similarly, a relay coil 282, when current flows therethrough, is coupled to move switch arm 268 from terminal 274 to terminal 272 and switch arm 270 from terminal 278 to terminal 276. One end of each of coils 280 and 282 is coupled to a source of positive voltage and the other end of each of coils 280 and 282 is coupled through the collector emitter path of respective transistors 284 and 286 to ground. As connected, coils 280 and 282 have current flow when the respective transistors 284 and 286 are rendered conductive by current flow towards into the respective bases thereof.

The base of transistor 286 is coupled to the output of NOR gate 288, which has its two inputs coupled to the /REV from output latches 184 and the SYSINHIBIT signal from main processor 178. Thus, coil 280 is energized only when it is desired to run the injector motor 176 in reverse, as manifested by the /REV signal being high and the SYSINHIBIT signal being low.

The base of transistor 286 is coupled to the output of three input AND gate 290; one input to AND gate 290 has the RUN signal from output latches 184 coupled thereto and another input of AND gate 290 has the /SYSINHIBIT signal, provided by passing the SYSINHIBIT through inverter 292, applied thereto. The third input of AND gate 290 is coupled to the output of overcurrent and overvoltage protection circuit 294. Protection circuit 294 monitors two signals MT1 and MT2 (described hereafter) from motor 176 to assure that the speed and back pressure of the injector system are not over limits. If either the speed or pressure become over limits during normal operation of injector motor 176 (RUN and /SYSINHIBIT are high), then detection circuit 294 provides a high signal to AND gate 290, thereby causing a high signal therefrom which energizes coil 282. This in turn switches switch arms 268 and 270 to contact terminals 274 and 278 and thereby removes the application of power to injector motor 176.

The drain of FET transistor 250 is coupled to terminals 262 and 264 of reverse relay 252. The back EMF of injector motor 176 is proportional to the speed of injector motor 176 and appears as the voltage at the drain of FET transistor 250; this voltage is designated as the MT2 voltage signal. Terminals 260 and 266 of reverse relay 252 are coupled together and through a very small, such as 0.1 ohm, resistor 296 to ground, thereby permitting the current through motor 176 to be measured. This current is proportional to the back pressure of injector system 104. The junction between terminals 260 and 266 and resistor 296 is the MT1 voltage signal and manifests the current through motor 176.

The upper input of pulse width modulator 246 is the sum of three different signals provided through respective commonly connected scaling resistors 298, 300 and 302. The other end of resistor 198 has the VDC signal from the output of injector DAC 192 (FIG. 12) connected thereto and represents the primary signal (in the absence of detected speed or pressure error conditions) for controlling modulator 246. The other end of resistor 300 is connected to the output of a speed monitor circuit 304 which senses the back emf of injector motor 176. Speed monitor circuit 304 has the MT1 and MT2 signals applied to a differential amplifier therein, the output of which is a voltage signal proportional to the speed of injector motor 176. The other end of resistor 302 is provided through an analog inverter 306 to the output of a pressure detection circuit 308. Pressure detection circuit 308 responds to the MT1 signal and provides a negative voltage which is proportional to the current through motor 176 and the pressure buildup in syringe 120. The polarity of this voltage is inverted by inverter 306 and functions as a winding voltage drop compensation signal.

The lower input to pulse width modulator 246 is sum of two signals provided through commonly connected resistors 310 and 312. The other end of resistor 310 is connected to the pressure detection circuit 308 and the other end of resistor 312 is connected to selector circuit 314. Selector circuit 314 provides one of three different voltages, as determined by the settings of potentiometers 316, 318 and 320, to its output, as determined by the code of the REV and HI/LO signals provided to the selector inputs thereof. The REV signal is the /REV signal provided through inverter 322. The center tap arm of potentiometer 316 is connected to the first and second data inputs of selector circuit 314 and is coupled as the output of selector circuit 314 whenever the /REV signal is low, thereby indicating reverse direction movement of injector motor 176. The voltage from the center tap arm of potentiometer 318 appears at the output of selector circuit 314 if the /REV signal is high, thereby indicating forward movement of injector motor 176, and the HI/LO signal is high and the voltage from the center tap arm of potentiometer 318 appears at the output of selector circuit 314 if the /REV signal is high and the HI/LO signal is low. The particular signal appearing at the output represents the selected pressure permitted for fluid injector system 104, as determined by the operator's selection of the keys on operator's panel 116.

The junction of resistors 310 and 312 is also coupled to comparator 324 which provides the PRSFST signal to main processor 178 whenever the injector system 104 pressure has almost reached the limit as set by the operator. The output of comparator 324 is also provided to a one second timeout circuit 326, which provided the PRSSLO signal if the PRSFST signal remains high for more than one second.

In operation, the speed demand signal VDC from injector DAC 192 is summed with the speed signal from speed monitor 304 and the compensation signal from inverter 302 and applied to the upper input of pulse width modulator 246. At the same time, the pressure signals are provided to the lower input of modulator 246. Modulator 246 responds to the higher voltage applied thereto and decreases the duty cycle accordingly. This, in turn, reduces the speed of the injector motor 176.

Referring to both FIGS. 12 and 15, the speed of injector motor 176 is controlled as described below. When foot switch 108 is pressed, a software timer within main processor 178 is set to a frequency based upon the programmed flow rate information on display 134 of operator panel 116. The timeout signals from the software timer are compared with the EDGE signals from gate 244 in FIG. 14, which are related to the actual speed of motor 176, as detected from encoder wheel 174. Each time the software timer times out, a stored speed demand value is incremented by one bit and shortly thereafter the value stored in the speed demand register is provided over data bus 184 to injector DAC 192. At the same time, the SELDA2 signal is provided to enable injector DAC 192 to receive the new data bus 184 data signal.

Whenever an EDGE signal is detected, the encoder 174 phase signals, PHASEA and PHASEB, are decoded to determine whether forward or reverse motor shaft 175 rotation is occurring. If forward rotation is occurring, then the speed demand register is decremented by one bit. If reverse rotation of shaft 175 is detected while the RUN signal is on, thereby indicating motor jitter, then the speed demand register is incremented by one bit to cancel the corresponding forward pulse. As injector motor 176 comes up to speed, the speed demand value will increase exponentially as the increments caused by the timer timeout are cancelled more and more by the higher rate of EDGE pulses resulting from increasing speed.

During normal forward operation, an increase in the load will cause a corresponding decrease in speed. This is offset by an increase in the speed demand value and the injector DAC 192 output voltage. If the allowable pressure is reached, the FRSFST signal is issued. Main processor 178 responds to the PRSFST signal by not increasing the speed demand value, and hence the injector DAC 192 output value any further. If the PRSFST signal persists for one second, the PRSSLO signal is issued and main processor 178 shuts system 100 down.

In addition, if main processor 178 attempts to increase the speed of injector motor 176 and no speed increase response is detected in monitoring the EDGE signals for one revolution, then main processor 178 shuts down the entire system. Thus, if detection circuit 294 detects an emergency over voltage or over current situation and causes the run relay 254 to close, thereby shutting off power to injector motor 176, main processor 178 will detect the injector motor slow down by longer EDGE signals and attempt to compensate by appropriate signals to catheter motor DAC 190. Upon finding an absence of response (since run relay 254 has been reset), main processor 178 issues commands to shut down the catheter motor 172 and the remainder of the system. At the same time, an error message is displayed on the display of operator panel 116. It should be noted that despite the fact the injector motor 176 has been shut down, fluid will continue to flow for several seconds until the line pressure is reduced to zero. This is more than sufficient time to reduce the speed of the catheter motor 172.

In general, the speed checking for the much higher speed catheter motor 172 is accomplished by speed processor 180. Speed processor 180 reads catheter motor 172 speed data provided over data bus 184 from main processor 178 at the time it is provided to catheter DAC 190. This data is compared with the SENSOR/2 signal provided to the Timer input of speed processor 180. Using a table to compare the demand and actual speed values, speed processor 180 provides an error signal over line 3 of port B if the difference between the two is greater than the equivalent of a set rpm value. If this signal persists for one and a half seconds, timeout circuit 200 will change states and deliver an error signal to Line 4 of Port B. This, in turn, results in the sending of the HISPDER signal to main processor 178, which, in turn, causes catheter motor controller 170 to shut off catheter motor 172.

The operation of the program within speed processor 180 will now be described. The first routine executed on application of power or reset is called RESET. This routine initializes the ports and stack and performs a RAM and ROM test. Thereafter, it initialized itself with a speed request of zero and configures and starts the internal timer. A zero speed request is done by loading the accumulator with the requested value and then causing a software interrupt. In this case, the requested value is zero. The timer is then set up to run on a logical AND of the timer input and the microprocessor's internal clock (1 MHz) so that it can cause an interrupt every time it counts down to zero. Finally, the RESET routine jumps into the middle of the SPDER routine (described hereafter) so that it does not flag a speed error and, instead, waits for the high to low to high transition from main processor 178 to return to the main loop.

The main loop is where speed processor 180 actually monitors the speed of the catheter motor 172. It is also important to note that there are sections in the loop that check if a hand shake is to be done. In order for the main loop to function properly, the internal eight bit timer is configured so that the clock incrementing it is based on the logical AND of the internal clock (or operating speed of one MHz) and the SENSOR/2 signal being applied to the Timer input. The SENSOR/2 signal has a 50% duty cycle whose period is two times that of the period of the SENSOR signal coming from the catheter motor 172. The SENSOR signal is not a 50% duty cycle, which is why its frequency is divided by two. This is convenient because the amount of time the timer input is high is the same time for the period of one complete cycle of the catheter motor 172. By using this value, the speed of catheter motor 172 can be tested. Since speed processor 180 cannot measure the time that the timer input is low, it makes sure that it does not stay low for too long. Speed processor 180 performs the speed check, and by taking two readings, a good average of the speed of the motor is achieved. In checking if it is within the speed tolerance, the software does an upper and lower check.

Whenever the speed is out of tolerance, speed processor 180 does not signal main processor 178 right away; rather it starts timeout circuit 200. After timeout circuit 200 is started, speed processor 180 keeps reading the speed of catheter motor 172. If it reads a speed that is within the tolerance, it resets timeout circuit 200 if it has not already timed-out. If timeout circuit 200 does time out before speed processor 180 can get a speed reading that is within tolerance, speed processor 180 notifies main processor 178 of the speed error condition by issuing the HISPDER signal.

There are two interrupts that are critical to the operation of the main loop. They are the SELDA1 interrupt coming from main procesor 178 and the internal timer interrupt. The SELDA1 interrupt from main processor 178 is an external interrupt which is signaled through the /INT line of speed processor 180. This interrupt occurs whenever main processor 178 sends a speed value over data bus 184 to catheter motor 172. Since speed processor 180 needs to know what speed value is requested, it also reads and stores the new speed value.

The timer interrupt occurs when the timer input bit is high and the timer times out. Since the timer input signal stays high much longer than the eight bit timer can count, the timer interrupt routine is geared to increase a counter location every time that the timer times out. This expands the total bits used to count the length of time that the timer input stays high to sixteen bits.

The remainder of this portion of the disclosure discusses the routines involved with the flow of the main loop, then the TIMER interrupt handler and finally the /INT interrupt handler. There is also another interrupt that is used by speed processor 180 called the software interrupt. It is only used during the RESET routine and is not of major importance to the operation of the system, but is discussed since it is part of the /INT interrupt handler.

The LOOP routine is the starting point where speed processor 180 spends most of its time. The first thing done is to check if main processor 178 wants to perform a handshake, as mentioned previously. Then, the LOOP routine checks if it has received two cycles of the SENSOR/2 signal from catheter motor 172. When two SENSOR/2 cycles have been received, the LOOP routine jumps to the CHECK routine to see if the received SENSOR/2 manifest that the catheter motor 172 is within the allowable speed range. Then, it controls a test pin to show that the waveform, as seen by speed processor 180, is low and it clears memory locations TPER and TPER +1 which are used to count how long it sees a low signal. Although this count is not accurate, speed processor 180 performs this count to ensure that the waveform into the timer input bit does not stay low for too long.

The WLOW routine is where the program of speed processor 180 spends its time when the timer input is low. This routine is used when speed processor 180 is getting ready to read the period of the signal from catheter motor 172 while it is low. The tasks that the WLOW routine performs are the following:

1. checks if main processor 178 requests a handshake;
2. resets the watchdog circuit;
3. checks if the timer input is low for too long;
4. checks if timeout circuit 200 has timed out;
5. loops if the timer input is still low; and
6. continues onto the WHIGH routine if it sees a high signal on the timer input.

The WHIGH routine is executed when the timer input is high. This routine is used when speed processor 180 is actually reading the period of the SENSOR/2 signal from catheter motor 172 while it is high. The tasks that this routine performs are the following:

1. checks if main processor 178 requests a handshake;
2. resets the watchdog circuit;
3. checks if the timer input is high for too long;
4. checks if the time-out circuit has timed out;
5. loops if the timer input is still high; and
6. branches to the LOOP routine to get ready to read another period if the timer input is low.

The ISLOW routine is called if the WLOW routine finds that the timer input is low too long. The ISLOW routine sets TVALH to reflect a slow speed reading. It then assumes that the catheter motor 172 was not running too fast and skips the code that checks for a "running too fast" condition by jumping into the section of the CHECK routine where it determines if catheter motor 172 is running too slow.

The CHECK routine is where the two acquired cycles are tested to determine if they are within the allowable speed range. It first checks if the signal is too fast; in other words, past the upper speed limit of catheter motor 172 operating tolerances. Next, it checks if the speed is below the lower speed limit. If the speed is within the speed tolerances, then the CHECK routine makes sure that all error flags are cleared. Before speed processor 180 gets a speed reading again, this routine waits for the input to the timer to be low. However, while waiting for the input to go low, the CHECK routine makes sure that the timer input does not stay high too long. When the input goes low the CHECK routine jumps back to the main loop.

Since the software timer operates in a way that it counts down, rather than up, speed processor 180 takes the value of zero and subtracts it from the value stored in the timer register TDR to get the period that is still stored in the timer register. As mentioned earlier, the actual counter for the period is expanded to sixteen bits by using memory location TVAL to keep track of the number of times that the timer times out. It is this value that is used to hold the high byte of the timer period. The contents of the low byte of the timer period is the value calculated using the timer register. These values are stored at locations TVALH and TVALL, respectively. Note that TVAL is updated by the timer interrupt routine and not by the main loop.

When a speed value is requested, the /INT routine sets up locations VFASTH/VFASTL and VSLOWH/VSLOWL to reflect the speed limits of the requested speed value. To check if the speed that is read is past the upper limit, locations TVALH/TVALL and VFASTL/VFASTL are compared to each other, respectively. If TVALH/TVALL are less than or equal to VFAST/VFASTL, then locations TVALH/-TVALL and VSLOW/VSLOWL are compared to each other, respectively. Then, if locations TVALH/-TVALL are greater than or equal to the values at locations VSLOWH/VSLOWL, the software in speed processor 180 manifests that there is no high or low speed error and it clears the hardware time-out circuit 200. However, if a speed error is detected, the timeout circuit 200 control bit is set high even if it was previously set.

Speed processor 180 then re-synchronizes itself on a low edge input of the SENSOR/2 signal to the timer input by setting the software timer register to $FF (as used herein, $ indicates "hexadecimal") to show that it has acquired zero period readings. The timer register is also reset and memory location TVAL is cleared to zero. At this point, if the timer input is low, speed processor 180 loops back to the main loop to get another speed reading for catheter motor 172. If the input is not low, the program checks if main processor 178 is requesting a handshake. Then, the watchdog one shot circuit 202 is reset. Next, location TVAL is checked to determine if the timer input is staying high for too long. If this is the case, further investigation is necessary; therefore, the software branches to the CHECK routine. If not, time-out circuit 200 is checked to see if it has expired. If the timer input bit is still high, the RSYNC routine is repeated with the exception of resetting the TVAL memory location and the timer register. If the timer input bit goes low, the RSYNC routine is called again only to properly reset the timer register and memory location TVAL and to ensure that the timer input is low.

The TOOSLOW routine is called during the CHECK routine, if the acquired speed reading is found to be below the acceptable lower tolerance limit. The purpose of TOOSLOW routine is to indicate a slow speed error occurred and to flag the error. To do this, the TOOSLOW routine sets the diagnostic bits and calls the MRG routine to actually flag the error.

The TOOFAST routine is called during the CHECK routine, if the acquired speed reading is found to be above the acceptable upper tolerance limit. The purpose of the TOOFAST routine is to show the world that a fast speed error occurred and to glag the error. To do this, the TOOFAST routine sets the diagnostic bits properly and calls MRG routine to actually flag the error.

The MRG routine flags a speed error condition. It first makes sure that the catheter motor 172 was stopped. To flag the speed error condition, the MRG routine does not actually show the error to main processor 178, rather it starts the time-out circuit 200. Then it jumps to the RSYNC routine to get another speed reading.

Every time the time-out circuit 200 is found to have expired, the SPDER routine is called to let main processor 178 know of the speed error condition. After sending notice of the speed error to main processor 178 by providing the HISPDER signal as a high value, the SPDER routine waits for main processor 178 to send notice to clear the speed error condition before it continues monitoring the speed of catheter motor 172 again. It is important to note that the SPDER routine is also used for performing the handshake between main processor 178 and speed processor 180, because it requires a high to low to high sequence before it resets a speed error.

In order to flag a speed error, the SPDER routine sets the speed error line high. Then it waits for the high to low to high sequence and then clears the speed error condition by clearing the speed error line, resetting the input to time-out circuit 200 and waiting for timeout circuit 200 to clear, re-enabling catheter motor 172, and jumping back into the section of the main loop that continues to monitor the speed of catheter motor 172.

The TSTLOW routine is designed so that, every time it is called, it consumes a fixed amount of time. It also checks how many times it is called. The carry bit is cleared to flag that the timer input, which is the same signal going into Bit 0 of Port B, has been low for too long. Otherwise, the carry bit is set to indicate that the signal is still acceptable. In order to keep track of how many times TSLOW is called the TSTLOW routine increases memory location TPER every time that it is called. It increases memory location TPER+1 every time the increasing of memory location TPER loops back to zero. It takes 80 microseconds (or 80 microprocessor clock cycles) to service the TSTLOW routine. The routine is allowed to be called $333 times (representing 70 ms). When location TPER reaches a value of $3, the carry flag is cleared before returning to the caller of the TST LOW routine; otherwise, it returns to the caller with the carry flag set.

Whenever a routine mentions resetting the watchdog circuit the WDOG routine is called to perform that task. In order for the WDOG routine to reset the watchdog circuit, it brings Bit 6 of Port B low and then high again.

The TIMER interrupt handler routine is responsible for the monitoring of the speed of catheter motor 172. This routine is called every time the internal eight bit timer times out so that it keeps track of the number of times that the timer times out and manifests when the timer times out. To do this, the timer interrupt handler first checks the value stored at location TVAL and checks if it has already been increased to $FF. If so, it does not increase TVAL anymore and manifests through the diagnostic timeout bit that a timeout has occurred. If TVAL is not at $FF, the TIMER interrupt handler routine increases TVAL by one and manifests that a timeout occurred, as mentioned previously.

The SELDA1 line coming from main processor 178 that is tied to the of catheter motor DAC 192 is also tied to the interrupt request line /INT of speed processor 180. Since the SELDA1 signal is active low, speed processor 180 is interrupted every time that a speed value is latched on the catheter motor DAC 192. Since there is a possibility that a speed value might be sent while speed processor 180 is servicing the timer interrupt, as mentioned previously, a handshake is performed to ensure that speed processor 180 got the new speed value. In addition to getting the requested speed value, the /INT routine sets up the proper values at memory locations VSLOWL/VSLOWH and VFASTL/VFASTH. Setting up these memory locations is the portion of the /INT routine that makes up the software interrupt handler. This section of the /INT routine is called SOFT.

The very first thing that the /INT routine does is to get the speed data value sent to Port A. This is the same value that is sent to the catheter motor DAC 192. Then the /INT routine checks if this is a valid value by checking whether or not the /INT line is active. If the /INT line is inactive, the /INT routine does not accept the value on Port A as a valid speed request value and exits. If the /INT line is active, the /INT routine accepts the value to be valid and speed processor 180 lets main processor 178 know that speed processor 180 has acquired the new speed value by setting the speed error line. This is the beginning of the handshake sequence between the two processors that verifies speed processor 180 has received the newly requested speed value. Then the /INT routine clears time-out circuit 200 to prevent a time-out from occurring. The /INT routine then waits for main processor 178 to deactivate the /INT line. While waiting for the /INT line to be deactivated, watchdog circuit 202 is continuously being reset. Note that the WDOG routine is not called to reset the watchdog, rather the necessary code is inserted in the loop for timing purposes.

When main processor 178 deactivates the /INT line, it tells speed processor 180 that main processor 178 has received notice that the speed value was received. This is the second phase of the handshake sequence. Since speed processor 180 uses the speed error line to do the handshake, speed processor 180 must deactivate the speed error line so that main processor 178 does not mistake it for a speed error. In the final phase of the handshake routine, main processor 178 waits for this line to be deactivated.

The SOFT routine sequence can also be interpreted as the software interrupt request handler/routine. The purpose of the SOFT routine is to generate offsets into the SLOWTAB and FASTTAB tables to retrieve the tolerance values for the requested speed value. The values retrieved will be stored in the proper memory location. It is the responsibility of the CHECK routine to determine if the detected speed value falls within these tolerance values.

In order to retrieve the tolerance values, the offsets must first be calculated. Note that since the offset points to two bytes and not one, it has to be multiplied by two. The calculated offset is stored at location WRO and location WRO+1. Next, the starting address of the SLOWTAB is added to this offset and is stored as the operand for the "LDA $XXXXX" command in RAM. After the addresses are properly set up, GETINI is called to ensure that the proper opcodes are stored in the proper RAM locations so that a jump to GET can be performed. Following the initialization of the proper RAM locations, the GET routine is called to get the high byte of the lower limit for the requested speed value. After the byte has been retrieved, it is stored in memory location VSLOWH. Then, INCGET is called to increase the address of the operand for the "LDA $XXXXX" command stored at memory location GET. This points to the low-byte of the lower limit for the requested speed value which is stored in locations VSLOWL. The same procedure is performed to get the upper tolerance limit bytes from FASTTAB except that they are stored in memory locations VFASTH and VFASTL instead of VSLOWH and VSLOWL. This then marks the end of the /INT routine so the routine returns to wherever the processor was interrupted.

In summarizing the operation of speed processor 180, it contains three basic routines, the main loop, timer interrupt handler routine, and the interrupt request/interrupt handler routine. The timer routine performs the actual counting of the pulses returning from catheter motor 172. The interrupt request routine informs speed processor 180 of the new operating speed. The main loop then takes the speed value generated by the timer routine and compares it to the speed value set up by the interrupt request routine.

That which is claimed is:

1. An intravascular catheter comprising;
    (a) an elongated flexible jacket having opposed proximal and distal ends and a central passageway extending between the ends;
    (b) a working head located at the distal end of the jacket, including a canalizing tip on the working head;
    (c) a drive cable extending through the central passageway and having a driving portion operatively located adjacent the distal end, and a driven portion located opposite the driving portion;
    (d) means for rotating the cable at the driven end; and
    (e) means for releasably coupling the driving end of the cable to the working head to rotate the tip wherein the cable may be uncoupled from the working head and removed from the jacket.

2. The catheter of claim 1 further comprising means for releasably coupling the proximal end of the jacket to the drive means.

3. The catheter of claim 1 wherein the working means is the cutting tip.

4. The catheter of claim 3 wherein the cutting tip includes a central guideway.

5. The catheter of claim 4 wherein the central guideway allows a guide wire or other probe to pass through the cutting tip.

6. The catheter of claim 1 wherein the drive cable comprises a flexible wire extending through the central passageway and having a driving portion operatively located adjacent the distal end, and a driven portion operatively located adjacent the proximal end.

7. The catheter of claim 1 wherein the drive cable is rotated at the driven end by a drive means.

8. An intravascular catheter comprising;
    (a) an elongated flexible jacket having opposed proximal and distal ends and a central passageway extending between the ends;
    (b) a working head located at the distal end of the jacket, including bearing means for supporting a rotatable canalizing tip on the working head, the tip including a central guideway and a drive shaft; and
    (c) a drive cable extending through the central passageway with a driving portion operatively located adjacent the distal end, and a driven portion located opposite the driving portion;
    (d) means for rotating the cable at the driven end;
    (e) means for infusing fluid through the central passageway;
    (f) means for releasably coupling the driving end of the cable to the working head to rotate the tip whereby the cable may be uncoupled from the working head and removed from the jacket and a guide wire inserted through the central passageway without removing the catheter from the lumen of a vessel.

9. The catheter of claim 8 wherein a proximal end of the driving portion is attached to the distal end of the drive cable.

10. The catheter of claim 8 wherein the removable drive cable is made of small diameter flexible cable having a proximal and a distal end, the distal end being attached to the driving portion and the proximal end of the cable being attached to a drive means, the drive cable is being further surrounded by a spirally wound bearing.

11. The catheter of claim 10 wherein the spiral bearing is a helical wire coil surrounding the drive cable and preventing it from contacting the catheter tube when the catheter tube is bent, the spiral bearing being removable from the catheter tube along with the drive cable as a single assembly.

12. The catheter of claim 8 wherein the proximal portion of the cable is coupled to the drive means.

13. The catheter of claim 9 wherein the driving portion is a torque-transmitting member.

14. The catheter of claim 8 wherein the central guideway in the tip and the driving portion are matable in shape.

15. The catheter of claim 14 wherein the driving portion is pushed forward into the central guideway, engaging and transmitting rotational torque to the tip.

16. The catheter of claim 14 wherein the drive portion is axially removable from the central guideway, disengaging the drive portion and the tip.

17. The catheter of claim 8 further comprising a luer-lock mechanism releasably coupling separable portions of the jacket to one another.

18. The catheter of claim 17 wherein the luer-lock mechanism comprises mating male and female connectors.

19. The catheter of claim 18 wherein the female connector is attached to proximal portion of the jacket and the male connector is attached to a distal portion of the jacket.

20. The catheter of claim 19 wherein the male and female connectors are readily engageable and disengagable, with one another, forming a quick-disconnect type joint between the proximal and distal ends of the jacket.

21. The catheter of claim 20 wherein the luer-lock mechanism provides an opening to remove the drive cable and insert a guide wire through the jacket central passageway without removing the catheter from the lumen of the vessel.

22. The catheter of claim 17 where in the luer-lock mechanism has a port for infusing fluid into the central passageway of the jacket.

23. The catheter of claim 8 wherein the rotatable tip is supported in a bearing which rigidly fixes the tip to the working head, while allowing the cutting tip to rotate within the bearing.

24. The catheter of claim 23 wherein the tip rotates at speeds up to 100,000 RPM.

25. An intravascular catheter comprising:
(a) an elongated flexible jacket composed of a pair of separable segments joined together at a point intermediate a pair of opposed proximal and distal ends of the jacket, including a central passageway extending between the ends;
(b) a working head located at the distal end of the jacket with a canalizing tip having a drive shaft, including bearing means for rotatably supporting the tip on the working head and a keyed guideway which extends through the drive shaft and communicates with the central passageway;
(c) means located at the proximal end of the jacket for rotating the tip at relatively high-speeds;
(d) means for releasably connecting the segments of the jacket together; and
(e) a removable drive assembly having a driving portion which releasably mates with the key way, a driven portion which is coupled to the drive means and a flexible drive cable extending between the driving and driven portions, allowing a guide wire to be inserted through the central passageway without removing the jacket from the vessel.

26. The catheter of claim 25, wherein the keyed guideway is torque-transmitting.

27. The catheter of claim 26, wherein the rotatable tip has flat sides forming a scraping edge for removing material from the wall of the lumen.

28. The catheter of claim 27, wherein driving the portion of the cable has an irregular polygonal shape with a rounded nose for ease of insertion into the key guideway and navigation through the catheter passageway.

* * * * *